United States Patent
Morris et al.

(10) Patent No.: US 7,838,841 B2
(45) Date of Patent: Nov. 23, 2010

(54) MEASURING MOMENTUM FOR CHARGED PARTICLE TOMOGRAPHY

(75) Inventors: Christopher Morris, Los Alamos, NM (US); Andrew Mcleod Fraser, Los Alamos, NM (US); Larry Joe Schultz, Los Alamos, NM (US); Konstantin N. Borozdin, Los Alamos, NM (US); Alexei Vasilievich Klimenko, Maynard, MA (US); Michael James Sossong, Los Alamos, NM (US); Gary Blanpied, Lexington, SC (US)

(73) Assignee: Los Alamos National Security, LLC, Los Alamos, NM (US)

( * ) Notice: Subject to any disclaimer, the term of this patent is extended or adjusted under 35 U.S.C. 154(b) by 124 days.

(21) Appl. No.: 11/977,410

(22) Filed: Oct. 24, 2007

(65) Prior Publication Data
US 2008/0265156 A1 Oct. 30, 2008

Related U.S. Application Data

(60) Provisional application No. 60/855,064, filed on Oct. 27, 2006.

(51) Int. Cl.
*H01L 25/00* (2006.01)
*H01L 27/00* (2006.01)
*G01T 1/29* (2006.01)
*G01K 1/08* (2006.01)
*H01J 3/14* (2006.01)

(52) U.S. Cl. .................... 250/397; 250/370.1

(58) Field of Classification Search .......... 250/305, 250/397, 370.09, 390.04, 370.1, 370.08
See application file for complete search history.

(56) References Cited

U.S. PATENT DOCUMENTS

| | | | |
|---|---|---|---|
| 6,606,403 B2 * | 8/2003 | Freifeld | 250/559.14 |
| 7,470,905 B1 | 12/2008 | Goldberg et al. | |
| 7,531,791 B2 * | 5/2009 | Bryman | 250/266 |

(Continued)

OTHER PUBLICATIONS

Bolton, Tim "High Energy Muon momentum estimation from multiple Coulomb scattering in dense detectors" May 1997. 33pp hep-ex/9705007.*

(Continued)

*Primary Examiner*—Jack I Berman
*Assistant Examiner*—Brooke Purinton
(74) *Attorney, Agent, or Firm*—Ortiz & Lopez, PLLC; Matthew F. Lambrinos; Kermit D. Lopez

(57) ABSTRACT

Methods, apparatus and systems for detecting charged particles and obtaining tomography of a volume by measuring charged particles including measuring the momentum of a charged particle passing through a charged particle detector. Sets of position sensitive detectors measure scattering of the charged particle. The position sensitive detectors having sufficient mass to cause the charged particle passing through the position sensitive detectors to scatter in the position sensitive detectors. A controller can be adapted and arranged to receive scattering measurements of the charged particle from the charged particle detector, determine at least one trajectory of the charged particle from the measured scattering; and determine at least one momentum measurement of the charged particle from the at least one trajectory. The charged particle can be a cosmic ray-produced charged particle, such as a cosmic ray-produced muon. The position sensitive detectors can be drift cells, such as gas-filled drift tubes.

8 Claims, 11 Drawing Sheets

U.S. PATENT DOCUMENTS

2006/0180753 A1    8/2006    Bryman ..................... 250/266
2007/0102648 A1    5/2007    Shpantzer et al.

OTHER PUBLICATIONS

Borozdin, Konstantin et al., "Cosmic-Ray Muon Tomography and Its Application to the Detection of High-Z Materials", Proceedings of the 46th Annual Meeting, Institute of Nucelar Materials Management, 2005, pp. 1-8.

Van Eijik, Carl W.E., "Neutrons PSD's for the Next Generation of Spallation Neutron Sources" Nuclear Instruments and Methods in Physics Research A, 2002, vol. 477, pp. 383-390.

Zhao, T. et al. "Do Forward-Angle Muon Tracking Detector and Its Gas System", IEEE Transactions on Nuclear Science, Jun. 2002, vol. 49, No. 3 pp. 1092-1096.

Byrd, Roger C. et al. "Nuclear Detection to Prevent or Defeat Clandestine Nuclear Attack", IEEE Sensors Journal, Aug. 2005, vol. 5, No. 4, pp. 593-609.

Zhou, Bing, "Large Precision Muon Detector for ATLAS", Nuclear Instruments and Methods in Physics Research A, 2002, vol. 494, pp. 464-473.

Hengartner, Nicolas et al., Information Extraction for Muon Radiography, Nuclear Science Symposium Conference Record, 2005 IEEE, vol. 1, Oct. 28-29, 2005, pp. 11-15.

Fessler, Jeffery A. "Statistical Methods for Image Reconstruction" (annotated slides for attendees of the NSS-MIC short Course), Oct. 24, 2004.

Schultz, L. J. et al., "Image Reconstruction and Material Z Discrimination via Cosmic Ray Muon Radiography", Nuclear Instruments and Methods in Physics Research A, 2004, vol. 519, pp. 687-694.

Jenneson, P.M. "Large Vessel Imaging Using Cosmic-ray Muons", Nuclear Instruments and Methods in Physics Research A, 2004, vol. 525, pp. 346-351.

Fessler, Jeffery A., "Penalized Maximum-Likelihood Image Reconstruction Using Space-Alternating Generalized EM Algorithms", IEEE Transactions on Image Processing, 1995, vol. 4 No. 10, pp. 1417-1429.

PCT—Notification of Transmittal of the International Search Report and the Written Opinion of the International Searching Authority, or the Declaration, Date of Mailing, Dec. 24, 2008.

A Terrorist Threat—The Movement of Black Market Nuclear Materials into the United States; Gene R. Kelley, Nov. 17, 2001; www.wagingpeace.org/articles/2001/11/17_kelley_terrorist-threat.htm.

Radiographic Imaging with Cosmic-Ray Muons; K.N. Borozdin, G.E. Hogan, C. Morris, W.C. Priedhorsky, A. Saunders, L.J. Schultz, M.E. Teasdale; Los Alamos National Laboratory; vol. 422, Mar. 20, 2003, www.nature.com/nature.

Detection of High-Z Objects Using Multiple Scattering of Cosmic Ray Muons; W.C. Priedhorsky, K.N. Borozdin, G.E. Hogan, C. Morris, A. Saunders, L.J. Schultz, M.E. Teasdale; Review of Scientific Instruments, vol. 74, No. 10, Oct. 2003.

Cosmic Ray Muon Radiography; Larry J. Schultz; Dissertation for Ph.D. Electrical and Computer Engineering, Portland State University 2003.

Image Reconstruction and Material Z Discrimination Via Cosmic Ray Muon Radiography; L.J. Schultz, K.N. Borozdin, J.J. Gomez, G.E. Hogan, J.A. McGill, C.L. Morris, W.C. Priedhorsky, A. Saunders, M.E. Teasdale; NIM Submission Draft—Jun. 30, 2003.

Convergent Incremental Optimization Transfer Algorithms: Application to Tomography; S. Ahn, J.A. Fessler, D. Blatt, A.O. Hero; IEEE Transactions of Medical Imaging, vol. 25, No. 3, Mar. 2006.

Geant4 Developments and Applications; J. Allison, K. Amako, J. Apostolakis, H. Araujo, P. Arce Dubois, M. Asai, G. Barrand, R Capra, S. Chauvie, R. Chytracek, G.A.P. Cirrone, G. Cooperman, G. Cosmo, G. Cuttone, G.G. Daquino, M. Donszelmann, M. Dressel, G. Folger, F. Foppiano, J. Generowicz, V. Grichine, S. Guatelli, P. Gumplinger, A. Heikkinen, I. Hrivnacova, A. Howard, S. Incerti, V. Ivanchenko, T. Johnson, F. Jones, T. Koi, R. Kokoulin, M. Kossov, H. Kurashige, V. Lara, S. Larsson, F. Lei, O. Link F. Longo, M. Maire, A. Mantero, B. Mascialino, I. McLaren, P. Mendez Lorenzo, K. Minamimoto, K. Murakami, P. Nieminen, L. Pandola, S. Parlati, L. Peralta, J. Perl, A. Pfeiffer, M.G. Pia, A. Ribon, P. Rodrigues, G. Russo, S. Sadilov, G. Santin, T. Sasaki, D. Smith N. Starkov, S. Tanaka, E. Tcherniaev, B. Tome, A. Trindade, P. Truscott, L. Urban, M. Verderi, A. Walkden, J.P. Wellisch, D. C. Williams, D. Wright, H. Yoshida; IEEE Transactions on Nuclear Science, vol. 53, No. 1, Feb. 2006.

Maximum Likelihood from Incomplete Data Via the EM Algorithm; A.P. Dempster, N.M. Laird, D.B. Rubin; Journal of the Royal Statistical Society. Series B, vol. 39, No. 1. (1977), pp. 1-38.

Passage of Particles Through Matter; H. Bichsel, D.E. Groom, S.R. Klein; http://pdg.lbl.gov/; Aug. 29, 2007.

Statistical Image Reconstruction for Polyenergetic X-ray Computed Tomography; I.A. Elbakri, J.A. Fessler; IEEE Transactions on Medical Imaging, vol. 21, No. 2, Feb. 2002.

Optimizing the Tracking Efficiency for Cosmic Ray Muon Tomography; J. Andrew Green, C. Alexander T. Asaki, J. Bacon, G. Blampied, K. Borozdin, A. Canabal-Rey, M. Cannon, R. Chartrantd, D. Clark, C. Espinoza, E. Figueroa, A. Frazer, M. Galassi, J. Gomez, J. Gonzales, N. Hengartner, G. Hogan, A. Klimenko, P. McGaughey, G. McGregor, J. Medina, C. Morris, K. Mosher, C. Orum, F. Pazuchanics, W. Piedhorsky, A. Sanchez, A. Saunders, R. Schirato, L. Schultz, M. Sossong, M. Sottile, J. Tenbrink, R. Van de Water, K. Vixie, B. Wohlberg, 2006.

Multiple Coulomb Scattering and Spatial Resolution in Proton Radiography; U. Schneider, E. Pedroni; Med. Phys. 21 (11), Nov. 1994.

A Statistical Model for Positron Emission Tomography; Y. Vardi, L.A. Shepp, L. Kaufman; Journal of the American Statistical Association, vol. 80, No. 389. (Mar. 1985), pp. 8-20.

\* cited by examiner

MEASURING MOMENTUM FOR CHARGED PARTICLE TOMOGRAPHY

CROSS-REFERENCE TO PROVISIONAL APPLICATION

This application claims priority under 35 U.S.C §119(e) to the U.S. provisional patent application No. 60/855,064, entitled "Systems, Methods and Apparatus for Particle Detection and Analysis and Field Deployment of the Same", which was filed Oct. 27, 2006, the disclosure of which is incorporated herein by reference.

STATEMENT REGARDING FEDERAL RIGHTS

This invention was made with Government support under Contract Number DE-AC52-06NA25396 awarded by the United States Department of Energy. The Government has certain rights in the invention.

TECHNICAL FIELD

Embodiments relate to fields of particle detection, analysis, control and, more particularly but not exclusively, to methods and systems for analyzing data from a charged particle detection system having a plurality of drift tubes, chambers, or other particle detection devices and for measuring the momentum of a charged particle, such as a cosmic ray-produced muon, passing through the charged particle detection system.

BACKGROUND

Charged particle detection systems can be used to detect charged particles passing through a volume.

One such charged particle detector is a charged particle detector which tracks charged particles including cosmic ray-produced muons or other charged particles. Natural background cosmic ray-produced charged particles, such as muons, are generated by cosmic rays and are highly penetrating. Primary cosmic rays interact in the upper atmosphere, producing many particles including pions which decay into muons. Muons interact only through the Coulomb and weak forces. Muons arrive at a rate of about $1/cm^2/minute/steradian$. The muon's lifetime at rest is 2.2 microseconds. At the average energy of 3 GeV, its relativistically time dilated lifetime is about 65 microseconds, corresponding to a path length of about 20 km. Since this is greater than the characteristic thickness (the scale-height, about 8 km) of the Earth's atmosphere and energy losses are slow (about 2 $MeVcm^2/gm$), most muons produced by cosmic-ray interaction in the upper atmosphere survive to the Earth's surface and are not stopped or absorbed in the air. In addition, they cannot be shielded by practical thicknesses of matter.

A system and method for measuring the momentum of charged particle needed. It is believed that the method and system of the illustrative embodiments provides an effective way of measuring the momentum of cosmic ray muon or other charged particles.

BRIEF SUMMARY

The following summary of the invention is provided to facilitate an understanding of some of technical features related to techniques, apparatus and systems for determination of the momentum of a charged particle and for detecting particles such as charged particles like muons and is not intended to be a full description. Examples of methods, apparatus and systems are described for detecting charged particles and obtaining tomography of a volume by measuring charged particles including measuring the momentum of a charged particle passing through a charged particle detector. A full appreciation of the various aspects of the invention can be gained by taking the entire specification, claims, drawings, and abstract as a whole.

The aforementioned aspects of the invention and other objectives and advantages can now be achieved as described herein.

According to one aspect, a detection system is described for detecting an object volume via charged particles passing through the object volume. This system includes a first set of position sensitive detectors located on a first side of an object volume to measure positions and angles of incident charged particles towards the object volume; a second set of position sensitive detectors located on a second side of the object volume opposite to the first side to measure positions and angles of outgoing charged particles exiting the object volume; and a signal processing unit to receive data of measured signals from the first set of position sensitive detectors and measured signals from the second set of position sensitive detectors. The signal processing unit processes the received data to measure momenta of incident and outgoing charged particles.

According to another aspect, a method for measuring the momentum of a charged particle passing through a charged particle detector having a plurality of position sensitive detectors comprises: (a) configuring a plurality of position sensitive detectors to scatter a charged particle passing therethrough; (b) measuring the scattering of a charged particle in the position sensitive detectors; (c) determining at least one trajectory of the charged particle from the positional measurements; and (d) determining at least one momentum measurement of the charged particle from the at least one trajectory.

The method allows the momentum of the charged particle to be calculated from the trajectory of the charged particle as determined from the scattering of the charged particle in the position sensitive detectors themselves without the use of additional metal plates in the detector.

Measuring the scattering of a charged particle in the position sensitive detectors can include detecting position sensitive detectors hit by charged particles and corresponding hit times. Determining at least one trajectory of the charged particle from the positional measurements can comprise fitting one or more linear tracks to the positional measurements of the charged particle. Determining at least one momentum measurement of the charged particle from the at least one trajectory can comprise determining the momentum of the charge particle from the goodness of the linear track fit(s) or other measure of the linearity of the charged particle trajectory.

Configuring a plurality of position sensitive detectors to scatter a charged particle passing therethrough can comprise measuring the incident scattering of the charged particle passing through position sensitive detectors arranged on the incident side of an object volume; and measuring the exit scattering of the charged particle passing through position sensitive detectors arranged on the exit side of an object volume. Determining at least one trajectory of the charged particle from the positional measurements can comprise determining an incident trajectory of the charged particle from the measured incident scattering; and determining an exit trajectory of the charged particle from the measured exit scattering.

Determining at least one momentum measurement of the charged particle from the at least one trajectory can comprise determining an incident momentum measurement of the charged particle from the incident trajectory; and determining an exit momentum measurement from the exit trajectory.

The method can further comprise (e) averaging the incident momentum measurement and the exit momentum measurement in order to reduce noise.

Configuring a plurality of drift cells to scatter a cosmic ray charged particle passing therethrough can comprise providing sets of drift cells having mass sufficient to scatter the charged particle passing therethrough.

According to another aspect, a method for measuring the momentum of a cosmic ray charged particle passing through a detector having a plurality of drift cells comprises (a) configuring a plurality of drift cells to scatter a cosmic ray charged particle passing therethrough; (b) measuring the scattering of a cosmic ray charged particle in the drift cells, wherein measuring the scattering comprises obtaining at least three positional measurements of the scattering cosmic ray charged particle; (c) determining at least one trajectory of the cosmic ray charged particle from the positional measurements; and (d) determining at least one momentum measurement of the cosmic ray charged particle from the at least one trajectory.

According to another aspect, a system for measuring the momentum of a charged particle passing through a detector has a charged particle detector having position sensitive detectors, such as drift cells, with sufficient mass to cause the charged particle passing through the position sensitive detectors to scatter in the position sensitive detectors. The position sensitive detectors are also configured to obtain scattering measurements comprising at least there positional measurements of the charged particle. A controller, operably coupled to the charged particle detector, can be adapted and arranged to: receive scattering measurements of the charged particle from the charged particle detector. The controller can determine at least one trajectory of the charged particle from the measured scattering and can determine at least one momentum measurement of the charged particle from the at least one trajectory.

The plurality of position sensitive detectors can be arranged on at least one side of an object volume to be scanned.

The controller can be adapted and arranged to fit one or more linear tracks to the scattering measurements of the charged particle and determine the momentum of the charge particle from the goodness of the linear track fit(s) or other measure of the linearity of the charged particle trajectory.

The system can have a plurality of the position sensitive detectors arranged on the incident side of an object volume to be scanned to measure the incident scattering of the charged particle passing through the incident side position sensitive detectors. Another plurality of the position sensitive detectors can be arranged on the exit side of the object volume to measure the exit scattering of the charged particle passing through the exit side position sensitive detectors.

A controller can be adapted and arranged to determine an incident trajectory of the charged particle from the measured incident scattering and determine an exit trajectory of the charged particle from the measured exit scattering. The controller can be adapted and arranged to determine an incident momentum measurement of the charged particle from the incident trajectory; and determine an exit momentum measurement from the exit trajectory. The controller can be further adapted and arranged to average the incident momentum measurement and the exit momentum measurement in order to reduce noise.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION

Figure 1:
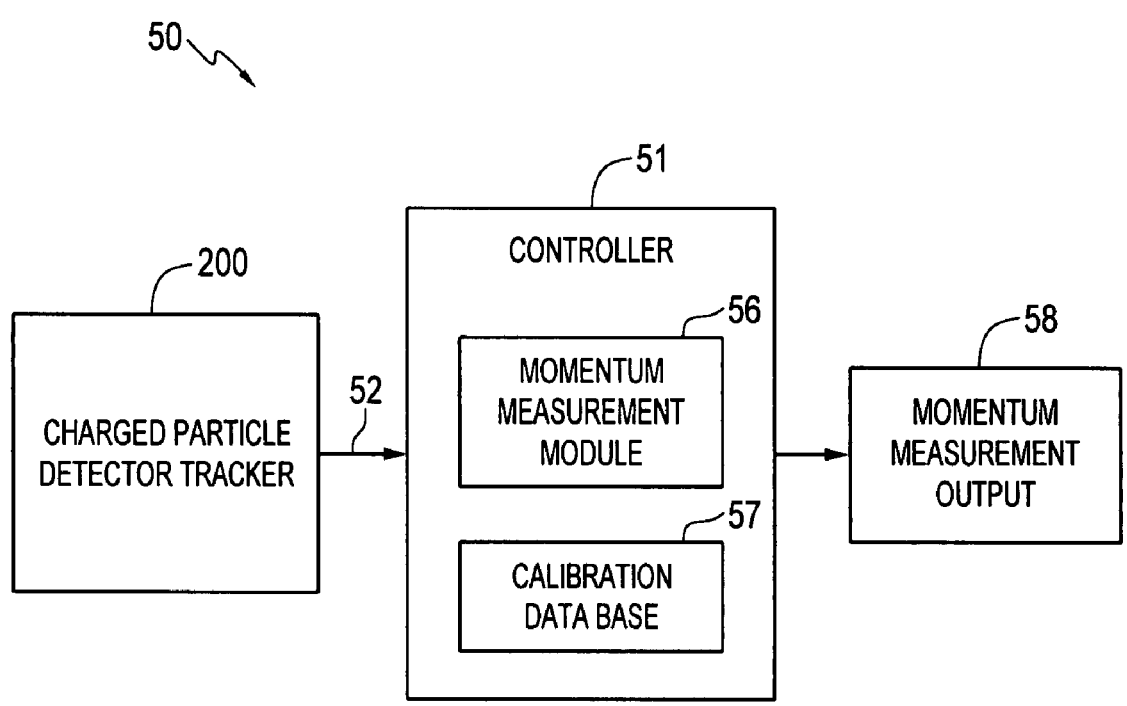
FIG. 1 illustrates a block diagram of a system for measuring the momentum of a charged particle passing through a charged particle detector, according to one embodiment.

The particular values and configurations discussed in these non-limiting examples can be varied and are cited merely to illustrate at least one embodiment of the present invention and are not intended to limit the scope of the invention.

Technical features described in this application can be used to construct various particle detection systems. For example, a particle detection system for detecting muons as the charged particles can include an object holding area for placing an object to be inspected, a first set of position sensitive muon detectors located on a first side of the object holding area to measure positions and angles of incident muons towards the object holding area, a second set of position sensitive muon detectors located on a second side of the object holding area opposite to the first side to measure positions and angles of outgoing muons exiting the object holding area, and a signal processing unit, which may include, e.g., a microprocessor, to receive data of measured signals of the incoming muons from the first set of position sensitive muon detectors and measured signals of the outgoing muons from the second set of position sensitive muon detectors. As an example, each of the first and second sets of particle detectors can be implemented to include drift tubes arranged to allow at least three charged particle positional measurements in a first direction and at least three charged particle positional measurements in a second direction different from the first direction. The signal processing unit is configured to analyze scattering behaviors of the muons caused by scattering of the muons in the materials within the object holding area based on the measured incoming and outgoing positions and angles of muons to obtain a tomographic profile or the spatial distribution of scattering centers within the object holding area. The obtained tomographic profile or the spatial distribution of scattering centers can be used to reveal the presence or absence of one or more objects in the object holding area such as materials with high atomic numbers including nuclear materials or devices. Each position sensitive muon detector can be implemented in various configurations, including drift cells such as drift tubes filled with a gas which can be ionized by muons. Such a system can be used to utilize natural cosmic ray muons as the source of muons for detecting one or more objects in the object holding area.

The processing of measurements for cosmic ray-produced muons in a volume under inspection (e.g., a package, a container or a vehicle) by the processing unit can include reconstructing the trajectory of a muon through the volume, measuring the momentum of an incoming muon based on signals from the detectors on each side of the volume, and determining the spatial distribution of the scattering density of the volume. These and other processing results can be used to construct the tomographic profile and measure various properties of the volume such as detecting a target object.

For example, the reconstruction of the trajectory of a charged particle passing through a detector having a set of drift cells can include (a) receiving hit signals representing identifiers of drift cells hit by charged particles and corresponding hit times; (b) grouping in-time drift cell hits identified as being associated with a track of a particular charged particle passing through the detector; (c) initially estimating time zero for the particular charged particle; (d) determining drift radii based on estimates of time zero, drift time conversion data and the time of the hit; (e) fitting linear tracks to drift radii corresponding to a particular time-zero; and (f) searching and selecting a time-zero value associated with the best of the track fits performed for particular charged particle and computing error in time-zero and tracking parameters. Such reconstruction of the track based on the time zero fit provides a reconstructed linear trajectory of the charged particle passing through the charged particle detector without having to use fast detectors (such as photomultiplier tubes with scintilator paddles) or some other fast detector which detects the passage of the muon through the apparatus to the nearest few nanoseconds to provide the time-zero.

Also for example, the processing for measuring the momentum of an incoming or outgoing muon based on signals from the detectors can include, for example, (a) configuring a plurality of position sensitive detectors to scatter a charged particle passing therethrough; (b) measuring the scattering of a charged particle in the position sensitive detectors, wherein measuring the scattering comprises obtaining at least three positional measurements of the scattering charged particle; (c) determining at least one trajectory of the charged particle from the positional measurements; and (d) determining at least one momentum measurement of the charged particle from the at least one trajectory. This technique can be used to determine the momentum of the charged particle based on the trajectory of the charged particle which is determined from the scattering of the charged particle in the position sensitive detectors themselves without the use of additional metal plates in the detector.

Also for example, the spatial distribution of the scattering density of the volume can be determined from charged particle tomographic data by: (a) obtaining predetermined charged particle tomography data corresponding to scattering angles and estimated momentum of charged particles passing through object volume; (b) providing the probability distribution of charged particle scattering for use in an expectation maximization (ML/EM) algorithm, the probability distribution being based on a statistical multiple scattering model; (c) determining substantially maximum likelihood estimate of object volume density using the expectation maximization (ML/EM) algorithm; and (d) outputting reconstructed object volume scattering density. The reconstructed object volume scattering density can be used to identify the presence and/or type of object occupying the volume of interest from the reconstructed volume density profile. Various applications include cosmic ray-produced muon tomography for various homeland security inspection applications in which vehicles or cargo can be scanned by a muon tracker.

In one aspect, the methods and systems for measuring the momentum of a charged particle through a charged particle detector according to the illustrative embodiments provide an approach in which scattering in a single set of tracking detectors can be used to accomplish a momentum measurement without having to employ additional plates between the detectors. Furthermore, the approach can be used to provide an average of the incident and exit momentum of a charged particle passing through an object volume so as to significantly reduce noise in reconstructions of the object scattering density.

Figure 10:
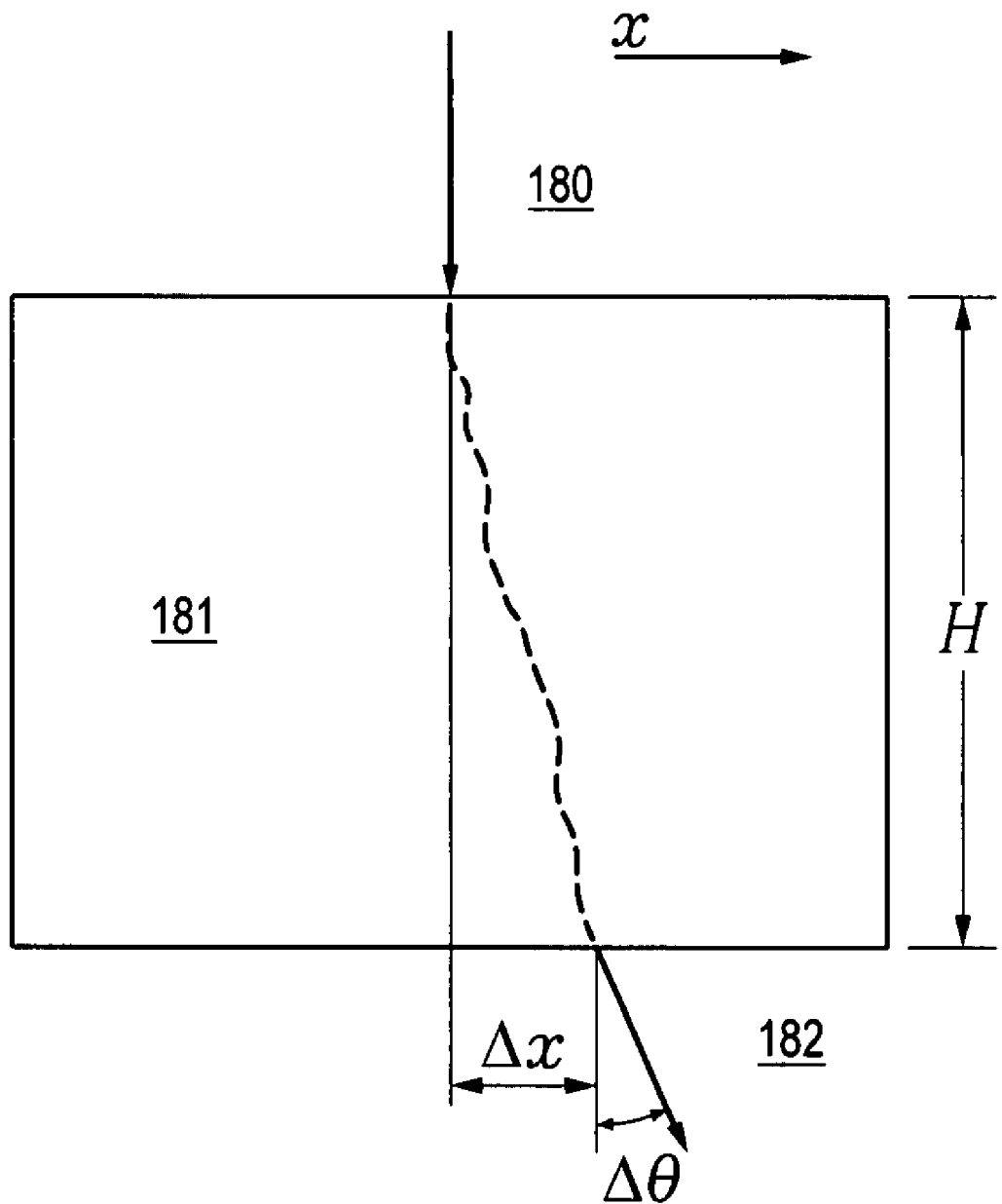
FIG. 10 illustrates a two-dimensional projection of scattering and displacement used to describe multiple Coulomb scattering.

A charged particle, such as a cosmic ray-produced muon, passing through material 181 experiences multiple Coulomb scattering as illustrated in FIG. 10, which illustrates a two-dimensional projection of scattering and displacement used to describe multiple Coulomb scattering. In this and other figures the magnitude of scattering is greatly exaggerated for illustrative purposes. The outgoing charged particle track 182 may be characterized by the scattering angle and displacement, taken relative to the orientation and position of the incident muon 180. Typical scattering angles are a few tens of milliradians (1 milliradian≈0.06 degrees), and scattering angles of more than a few degrees are very uncommon. The distribution of the central 98% of scattering angles may be approximated as a $$f_{\Delta\theta}(\Delta\theta) \cong \frac{1}{\sqrt{2\pi}\,\sigma_\theta} \exp\left(-\frac{\Delta\theta^2}{2\sigma_\theta^2}\right), \quad \text{Eq. (1)}$$

though the actual distribution has heavier tails with more large-angle scattering than a Gaussian. The width of the distribution may be expressed approximately in terms of material properties and the particle path length. Many researchers have presented empirically developed expressions for scattering as a function of various material properties, as reviewed in S. Eidelman et al., "Review of particle physics," *Phys. Lett.*, vol. B592, p. 1, 2004, the disclosure of which is incorporated herein by reference. A particularly simple form was presented by B. Rossi in *High Energy Particles*. Englewood Cliffs, N.J.: Prentice-Hall, 1952, the disclosure of which is incorporated herein by reference. This simple form is as follows:

$$\sigma_\theta \cong \frac{15\,\text{MeV}}{\beta c p} \sqrt{\frac{H}{L_{\text{rad}}}}. \quad \text{Eq. (2)}$$

Here, p is the particle momentum in MeV/c, H is the depth of the material, and $L_{rad}$ is the radiation length of the material. βc is velocity, where c is the speed of light and we will use an approximate value β=1. Radiation length decreases as atomic number and material density increase. We establish a nominal muon momentum, $p_0$, and define the scattering density of a material with radiation length $L_{rad}$, as $$\lambda(L_{\text{rad}}) \equiv \left(\frac{15}{p_0}\right)^2 \frac{1}{L_{\text{rad}}}. \quad \text{Eq. (3)}$$

The scattering density of unknown material can be determined by measuring the scattering of charged particles passing through that material. Though scattering density will affect the degree of charged particle scattering, it is clear from Eq. (2) that a particle's momentum will also affect it's scattering. If individual particle momenta may be measured, then the scattering of each particle may be normalized to provide a more precise scattering density estimate.

An example of an automated system for measuring the momentum of a charged particle according to one embodiment is illustrated in block diagram in FIG. 1. Automated system 50 has a controller 51 adapted and arranged to receive hit signals 52 from a charged particle detector 200 for tracking charged particles. A charged particle detector for tracking charged particles is defined herein to mean any charged particle detection system which utilizes position sensitive detectors configured to enable tracking of charged particles passing through a volume. The hit signals 52 are data collected from each position sensitive detector and represent: 1) time that the hit is collected by the electronics relative to a consistent but arbitrary origin, and 2) position sensitive detector channel number (or other identifier) of hit.

Automated system 50 includes a momentum measurement module 56 and calibration data base 57 stored on the controller. Predetermined drift cell positional information is stored in the calibration data base. Momentum measurement module 56 is responsible for measuring the momentum of the charged particle passing through the detector and providing a momentum measurement output 58. The module may be software or hardware.

In the illustrative embodiment of the automated system 50 of FIG. 1, the controller 51 is any kind of computer processor unit (CPU) based system such as a personal computer (PC), or other microprocessor based system such as a digital signal processor based system. An operating system runs on the controller 51 and may be a commercially available or open source operating system, such as (but not limited to) Apple, Windows, Unix, Linux or others not yet developed. Instructions for the operating system and applications or programs are stored in storage devices, such as a hard drive. A user interface (not shown) can be operably connected to the processing system to allow a human operator to manipulate the processing system, as required.

Also, in the automated system 50, the momentum measurement module 56 is software in the form of a computer-usable data carrier storing instructions that, when executed by the controller, cause the controller to perform a method of reconstructing the trajectory of a charged particle passing through a detector having a plurality of drift cells. The module can be installed locally on the controller, as indicated in FIG. 1, or run from a remote location via a network coupled to the controller. Those skilled in the art would understand there are multiple modes of implementing such a module.

Those skilled in the art would understand that the illustration of FIG. 1 is merely depicting one example of the embodiments and that the embodiments are not limited thereto. For example, some or all of the momentum measurement module functionality can be implemented as hardware such as analogue or digital circuitry without the use of microprocessor.

Figure 3:
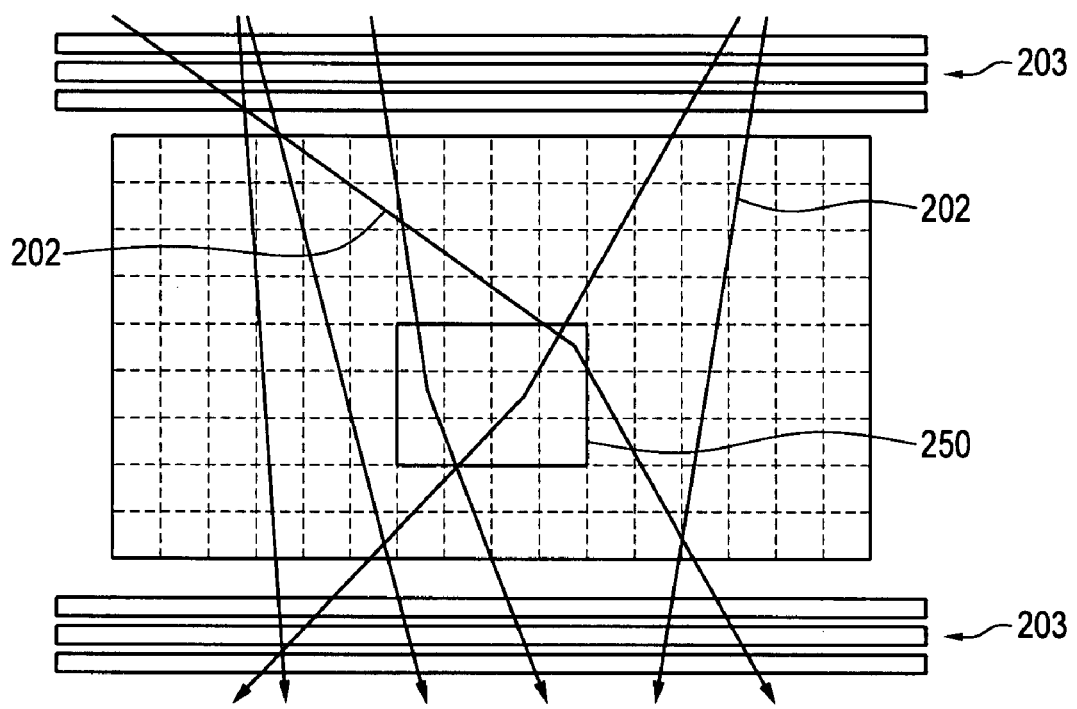
FIG. 3 illustrates a side view of the charged particle detector of FIG. 1

One example of charged particle detector 200 is depicted in FIG. 3, which illustrates a side view of position sensitive detectors 203 arranged above and below a volume occupied by an object 250 under interrogation. The position sensitive detectors 203 detect the incoming and outgoing charged particles which form tracks 202. On each side of the volume to be scanned, the drift tubes can be arranged to enable them to make at least three positional measurements in a first direction and in a second, different direction which may be orthogonal or non-orthogonal to the first direction In some implementations, additional drift tube detectors can be implemented on sides of the volume to form a box or four sided structure into which a package, a vehicle or cargo container can enter for scanning by the system.

A signal processing unit, e.g., a computer, is provided in the system to receive data of measured signals of the incoming muons by the detectors above the object volume and outgoing muons by the detectors below the object volume. This signal processing unit is configured to analyze scattering behaviors of the muons caused by scattering in the volume based on the measured incoming and outgoing positions and angles of muons to obtain a tomographic profile or the spatial distribution of scattering centers within the volume. The obtained tomographic profile or the spatial distribution of scattering centers within the volume can reveal the presence or absence of the object in the volume. Thus, multiple scattering of cosmic ray muons can be used to selectively detect high z-material in a background of normal cargo. Advantageously, this technique is passive, does not deliver any radiation dose above background, and is selective to high-z dense materials. The tomographic processing part of the signal processing unit may be implemented in an on-premise computer that is at the same location with the detectors. Alternatively, the tomographic processing part of the signal processing unit may be implemented in a remote computer that is connected on a computer network such as a private network or a public network such as the Internet.

As will be explained in more detail below, in order to measure the charged particle momentum, the charged particle position sensitive detectors of detector 200 have mass and so the particles will experience scattering in the detectors themselves. Referring to aforementioned Eq. (2), If H and $L_{rad}$ are fixed, then the degree of scattering is indicative of particle momentum. By estimating the degree of scattering in the particle detectors, particle momentum may be estimated. Any kind of other position sensitive detectors which have mass sufficient to cause the charged particles to scatter in the detectors themselves can be employed, or a slab of scattering material of known properties may be introduced.

For example, the position sensitive detectors 203 can be muon detectors employed for cosmic ray charged particle tomography of vehicles and cargo containers for homeland security applications. In such applications, the position sensitive detectors 203 must be large enough to fully encompass tractor-trailer trucks, vehicles of all sorts, and cargo containers.

Figure 2:
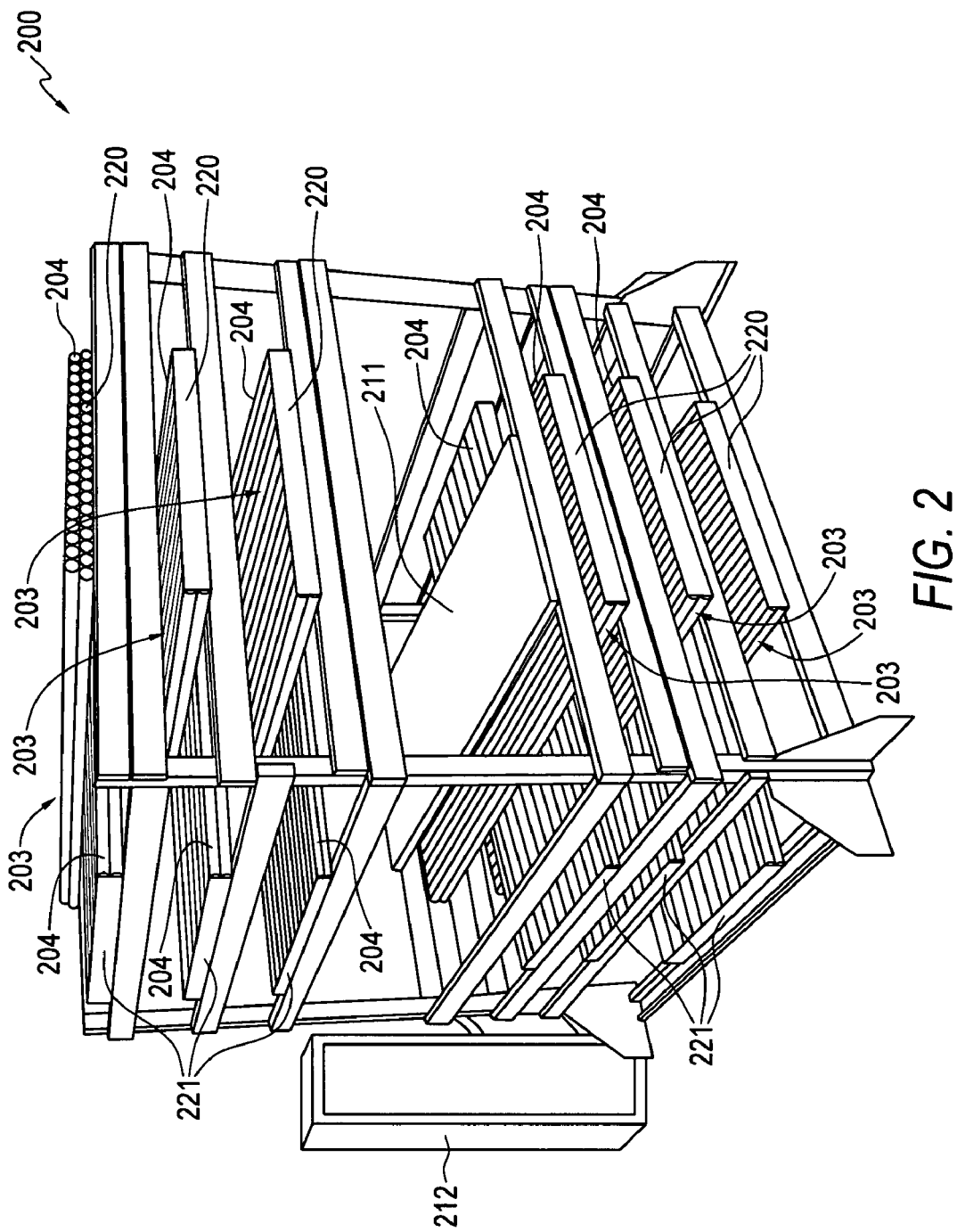
FIG. 2 illustrates a perspective view of an exemplary charged particle detector of the system of FIG. 1.

FIG. 2 illustrates a detailed perspective view of the charged particle detector 200 having sets of position sensitive detectors 203. Three sets of the position sensitive detectors 203 are arranged above the sample holder plane 211 and three sets of position sensitive detectors 203 are arranged below the sample holder plane 211. Each set of position sensitive detectors comprises a first double-layer 220 of drift tubes 204 arranged in the X direction and a second double-layer 221 of drift tubes 204 arranged in the Y direction. In each of the layers 220, 221, the drift tubes 204 are arranged in two rows, offset by half a tube diameter from each other.

In the system of FIG. 2, the drift tube modules can be 12 foot long aluminum drift tubes which are configured to measure the position and angle of incoming and outgoing muon tracks in X and Y coordinate directions. In each of the X and Y directions of each set of detectors 203, the drift tubes are arranged in two rows, offset by half a tube diameter from each other.

The tubes can be arranged in different ways. For example, the layers need not have to be 90 degrees from one another, but can be smaller non-zero angles. Also by way of example, the top layer could be at 0 degrees, middle layer at 45 degrees from the first, and a third layer 90 degrees from the first. This would allow resolution of multiple tracks that occur at the same instance of time.

Also, other position sensitive detector arrangements capable of scattering the charged particle passing therethrough and providing a total of at least three individual positional measurements can be adopted instead of the arrangement of detectors of FIG. 2. At least 3 position measurements are required so as to enable a line fit with a free parameter from which one can calculate momentum, Data acquisition electronics 212 record the hit time and channel number of the drift tubes, where a "channel" corresponds to each drift tube in the system.

One example of the data acquisition electronics 212, operably coupled to the drift tubes, will now be described. Drift tubes of the detector system 200 of FIG. 2 are connected to respective electronic amplifiers (not shown) which increase the voltage of the deposited signal (associated with a cosmic ray-produced muon passing through a drift tube). For each drift channel, the amplified signal is turned into a digital signal with a piece of electronics called a discriminator (on if there is a hit, off if no hit), which preserves the precise time of the hit. This combination of amplifier and discriminator is the "front-end" electronics. The time and channel number that the digital signal is registered to the nearest nanosecond by the time-to-digital-converters (TDCs) mentioned above. Each drift tube has its own front-end electronics and TDC.

The front-end electronics is built using hardware composed of off-the-shelf (OTS) parts. The TDC is OTS, and the units are built by Caen corporation in Italy. Each TDC unit (CAEN 767B) has the capability of 128 input channels (drift tubes in our case), and will store the time of the hit digitally. These units have a buffer which can hold about 32,000 hits. The TDCs are read-out about 5 times per second with a custom data-acquisition system (DAQ). The TDCs sit in a Versa Module Eurocard VME crate with a SIS 1100 controller, made by Struck Innovative Systeme GmbH (SIS), which provides the computer interface. The DAQ runs on a personal computer, with an optical cable to interface with the SIS 1100 to command the TDCs for the data transfer. Once the hit times and channel numbers are read out into the memory of the PC, the raw data is stored on hard drive, but the data is also processed to identify the cosmic ray events. The track data, and pertinent diagnostic data are also stored on the hard drive.

Figure 11:
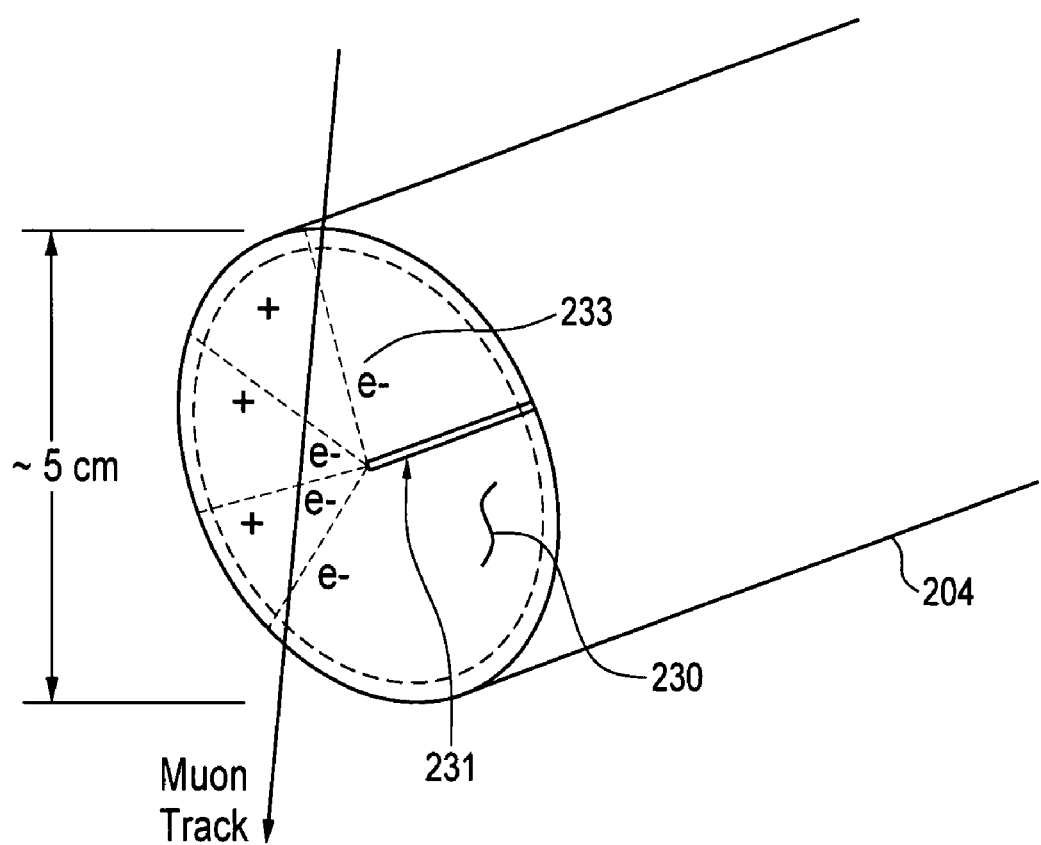
FIG. 11 illustrates a cross-section of a typical drift tube according to one embodiment.

A cross-sectional view of part of a typical drift tube 204 detecting a muon or other charged particle passing through the tube is illustrated in FIG. 11. The drift tube module is typically cylindrical and filled with a detector gas such as Argon-Isobutane 230 to enable detection of the cosmic ray-produced charged particles, such as muons. The system is configured to apply a positive HV of about +2-3 kV to a central anode wire 231 extending along the length of the cylindrical tube with the tube at ground so that a high-voltage static field is present. When the charged particle interacts with gas atoms, many electrons 233 are liberated from those atoms in a straight line through a chord of the tube. The static field causes the "string" of electrons to drift toward the positively charged anode wire. The anode wire is typically very thin, 0.001" in diameter, creating a very high field near the wire to produce an electron avalanche when the first electron arrives. The avalanche of charge is about $10^5$ electrons per incoming electron that are easily detected with sensitive electronics. The anode wire is read-out electronically with the TDCS (time-to-digital converters) of the data acquisition electronics 212. This is how a hit signal is produced when a charged particle moves through the detector drift tube.

Whilst the drift tube of FIG. 11 is manufactured from aluminum, other materials such as carbon composite with internal conductive coatings can be adopted instead of aluminum. The drift tubes need not have circular cross-sections. For example, the drift tubes may be constructed from aluminum extrusions with multiple, non-circular cross-sections. Alternatively, drift cells other than drift tubes can be adopted such as for example triangular shaped drift cells. Drift cells having many anode wires, such as small gas drift chambers (GDC), can be used instead of using drift cells having a single anode wire.

A typical operating set up of the detector 200 is as follows: 896 drift tube channels, drift gas 60% Ar/40% Isobutane, ~200 Hz trigger rate, 1.5 m tall sample area.

Figure 4A:
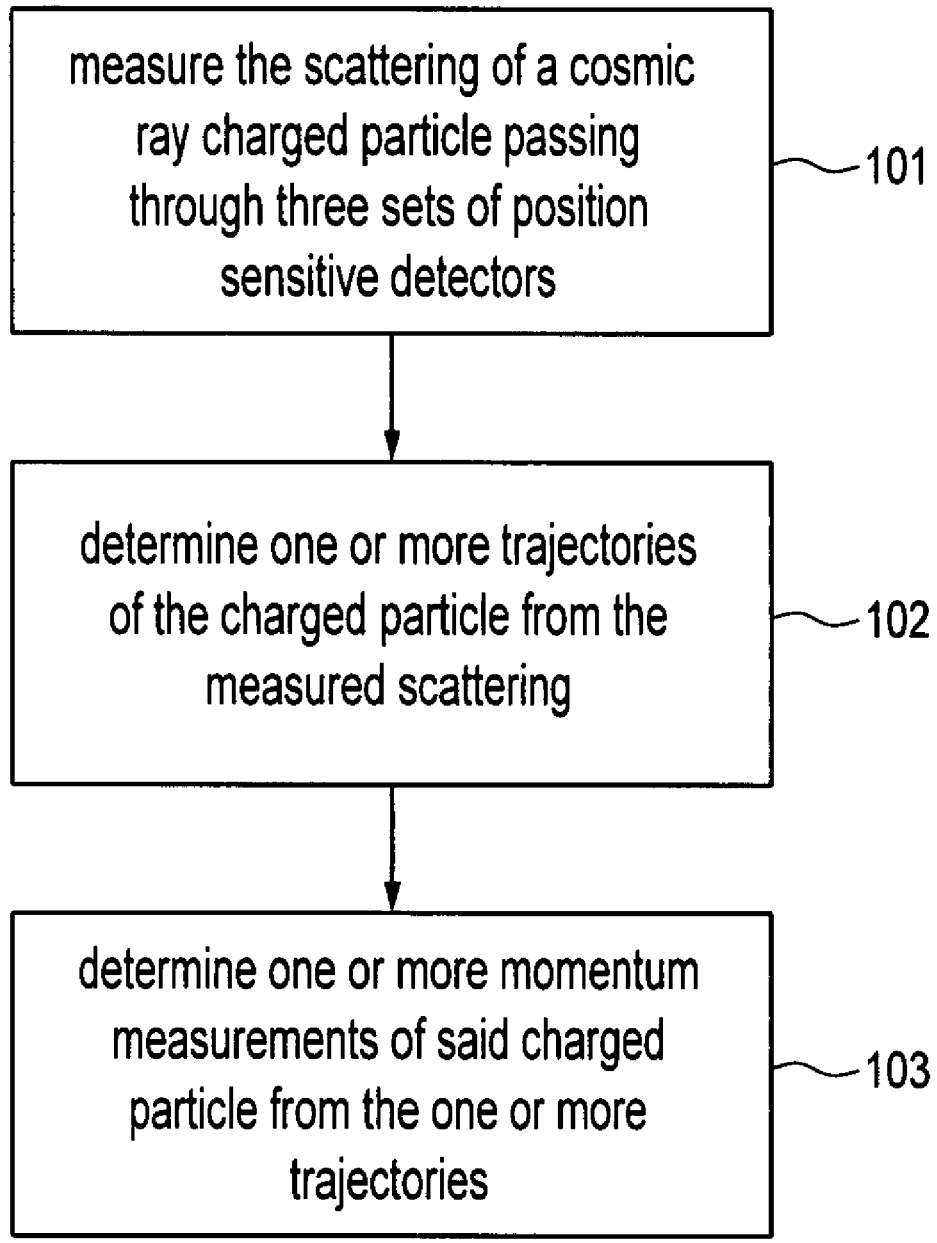
FIG. 4A illustrates a flow chart generally outlining a method of measuring the momentum of a cosmic ray-produced charged particle passing through a charged particle detector according to an embodiment.

A method for measuring the momentum of a charged particle passing through a charged particle detector according to one embodiment will now be described. FIG. 4A illustrates a flow chart generally outlining the method 100 for measuring the momentum of a charged particle passing through a charged particle detector. As indicated in process step 101, the scattering of a cosmic ray or other charged particle passing through charged particle position sensitive detectors is measured. To this end, the position sensitive detectors are configured to scatter the charged particle and obtain at least three positional measurements of the scattering charged particle passing therethrough. Thereafter, one or more trajectories of the charged particle is determined from the measured scattering, as indicated in process step 102. One or more momentum measurements of the charged particle are then determined from the one or more determined trajectories, as indicated in process step 103.

Providing sets of position sensitive detectors which scatter the charged particle and measuring the scattering of the charged particles in the position sensitive detectors themselves enables the momentum of the charged particle to be calculated from the trajectory of the charged particle as determined from the scattering measurements without the use of additional metal plates in the detector. In one implementation, this can be achieved without the use of additional metal plates in the detector.

The momentum is determined based on the lack of linearity of the measured trajectory of the charged particle. The momentum can be determined from residuals of the track fit or another measure of lack of linearity in the muon or other charged particle trajectory through the detection system. The momentum need not necessarily be determined based on residuals. The momentum can for example also be determined by fitting multiple tracks and looking at the angles between them.

Figure 4B:
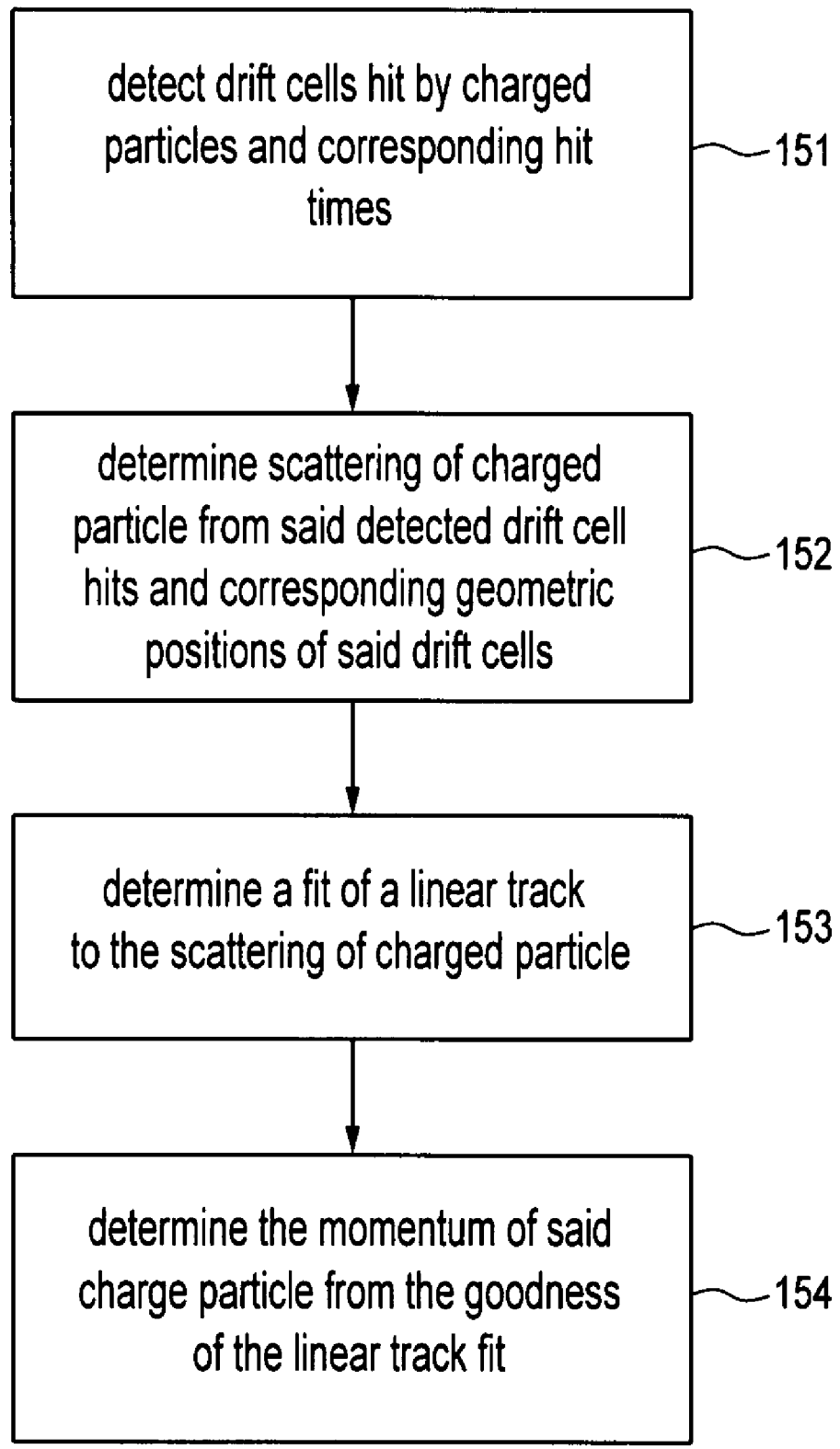
FIG. 4B illustrates a flow chart showing the method of FIG. 4A in more detail according to one embodiment.
Figure 6:
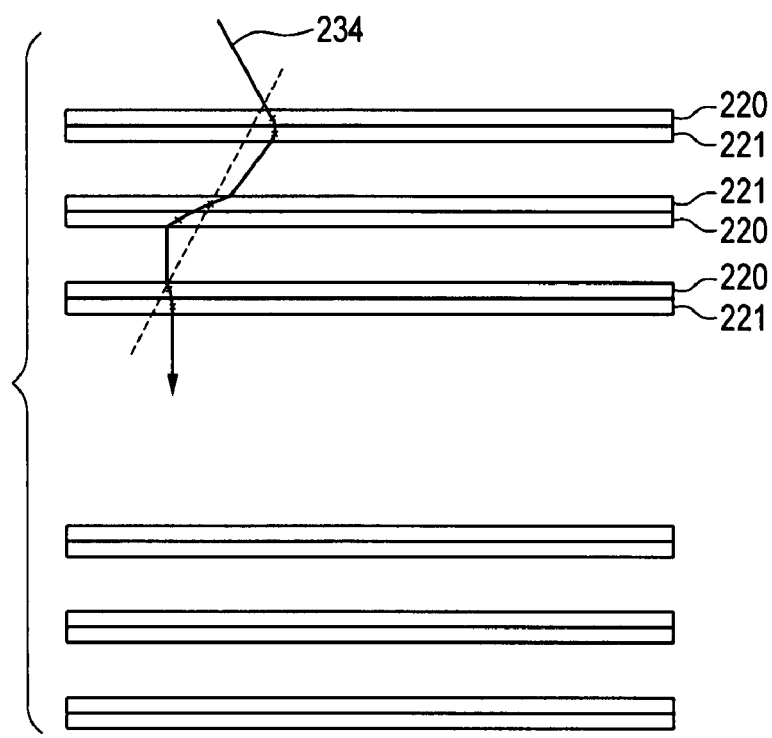
FIG. 6 illustrates a muon charged particle passing through three sets of drift cells of the muon detector of FIG. 2 according to one embodiment.
Figure 7:
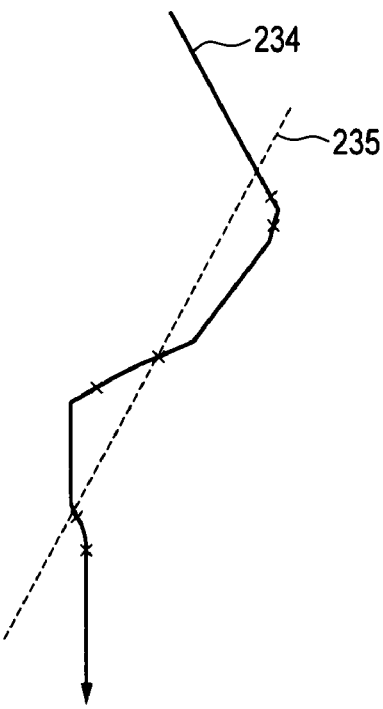
FIG. 7 illustrates an enlarged view of the scattering of the muon charged particle shown in FIG. 6.
Figure 8:
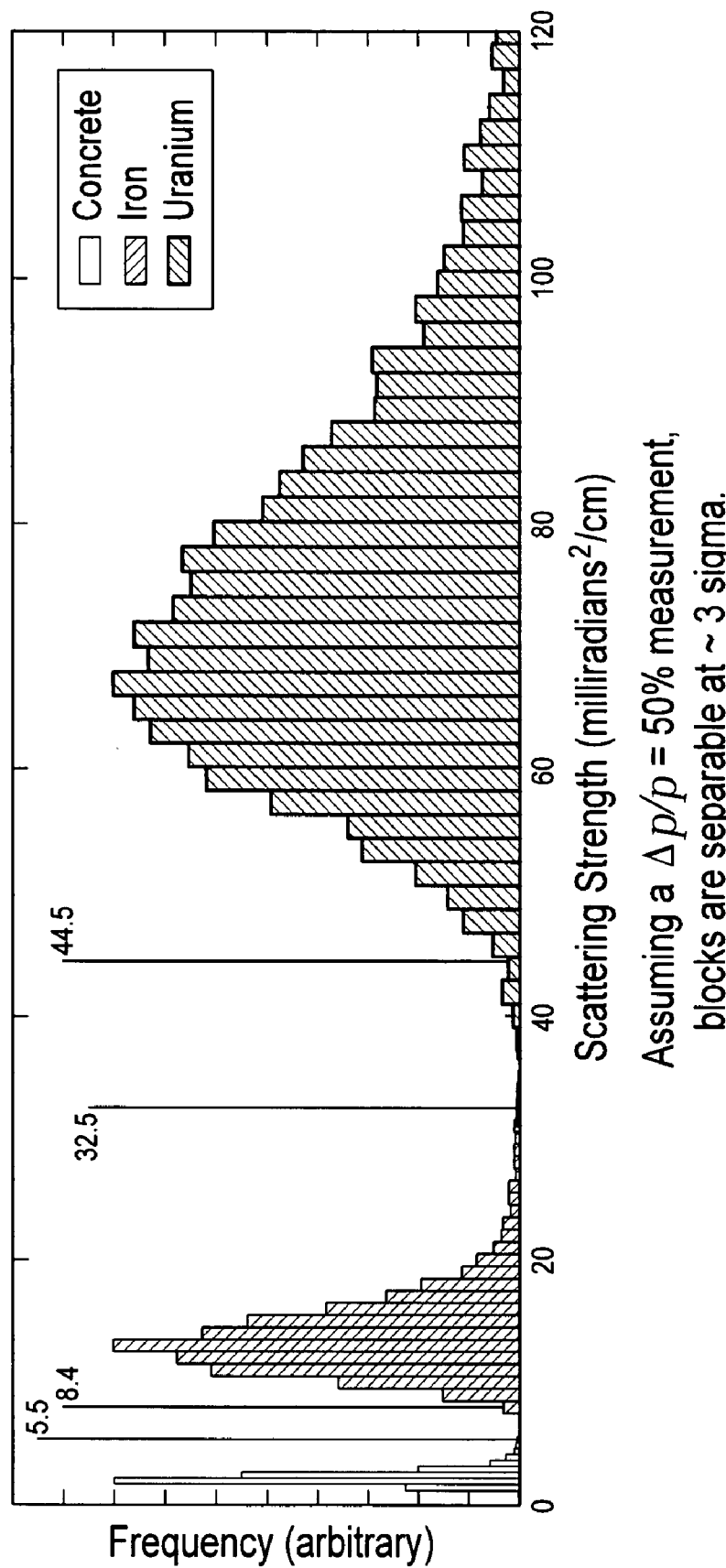
FIG. 8 illustrates a graph of the frequency distribution of inferred scattering strength for muons passing through concrete, iron and uranium assuming a rough ($\Delta p/p=50\%$) knowledge of momentum, showing that, for this approximate momentum measurement, the materials may be distinguished with negligible probability of confusion.

Method 100 of measuring the momentum of a charged particle according to one embodiment will now be described in more detail with reference to FIG. 4B. Method 100 can for example be implemented to measure the momentum of muon using the automated system of 50 of FIG. 1 in which the charged particle detector 200 is the muon detector of FIG. 2. FIG. 6 shows a typical example of the path 234 of a muon scattering as the muon passes through three sets of the drift cells of the detector 200 and FIG. 7 illustrates an enlarged view of the muon scattering shown in FIG. 6. Note that the particle track is not straight, since scattering occurs as the particle passes though the detector walls and other material in the volume. As each set of drift cells has a double layer 220 of X direction drift cells and a double layer 221 of Y direction drift cells, a muon passing through the detector will hit and scatter as indicated in FIGS. 6 and 7. The three sets of drift cells provide a total of six positional measurements. However, as already explained above, detector arrangements which can provide as few as 3 positional measurements can be adopted.

Detector 200 detects drift cell hits and corresponding hit times as a result of the muon passing through the drift tubes thereby implementing process step 151.

Controller 51 then determines the scattering of the muon through the three sets of drift cells based on which drift cells have been hit and their geometric positions so as to implement process step 152. The controller 51 obtains the hit signals 52 from the muon detector 200 and obtains their corresponding predetermined geometric positions. For example, the controller can reference the calibration database 57 using the drift cell channel numbers to retrieve the geometric positions of the respective hit drift cells. Thereafter, the momentum measurement module 56 fits one or more linear tracks (straight lines) through the scattering measurements so as to implement process step 153. Track fitting is accomplished using fitting of tracks to drift cell hits using least square fitting or other fitting methods. An example of such a linear track fit 235 to the path 234 of the scattering muon is shown in FIG. 7.

The momentum measurement module 56 then determines the momentum of the muon from the goodness of the linear track fit itself so as to implement process step 154. To this end, the module 56 determines the lack of straightness of the detector hits from residuals of the track fit and then determines the muon momentum. The multiple scattering of charge particles passing through matter leads to an approximately Gaussian angular distribution of trajectories whose width is proportional to the square root of the thickness traversed (measured in radiation lengths) and to the inverse of momentum. Accordingly, momentum can be determined using aforementioned Eqs. 1 & 2

Figure 5:
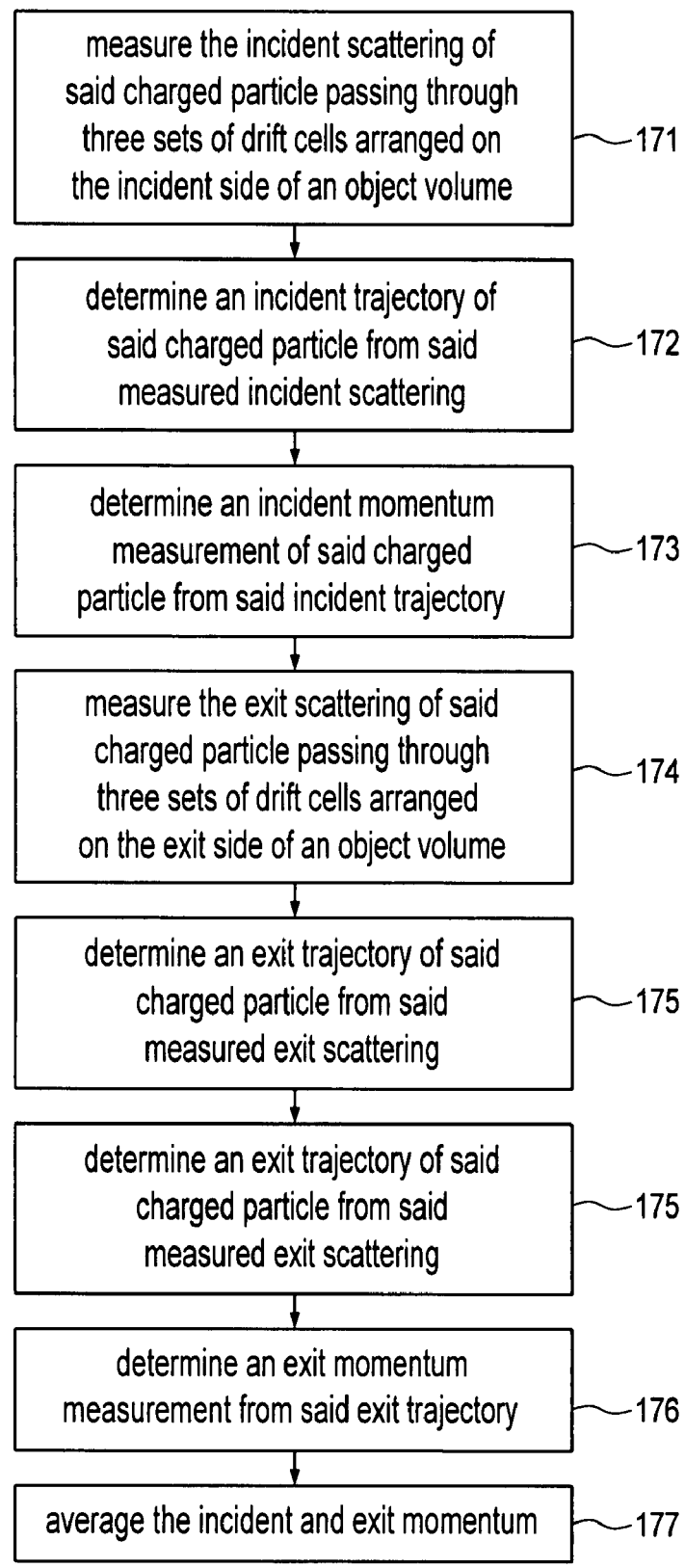
FIG. 5 illustrates a flow chart generally outlining a method of measuring the momentum of a cosmic ray-produced charged particle passing through a charged particle detector according to another embodiment.

A method 170 of measuring the momentum of a charged particle according to one embodiment will now be described in more detail with reference to FIG. 5 in which the incident and exit momentum of the charged particle is measured. Method 170 can for example be implemented to measure the momentum of a muon using the automated system of 50 of FIG. 1 in which the charged particle detector 200 is the muon detector of FIG. 2. FIG. 6 illustrates a typical example of the muon passing through three sets of drift cells arranged on the incident side of the detector 200 and another three sets of drift cells arranged on the exit side of the detector.

The incident scattering of the charged particle passing through three sets of drift cells arranged on the incident side of an object volume is first measured, as indicated in process step 171. In the automated system 50 of FIG. 1, process step 171 is implemented in the same manner as process steps 151 and 152 of method 100 of FIG. 4B. Thereafter, an incident trajectory of the charged particle is determined from the measured incident scattering path, as indicated in process step 172. In the automated system 50 of FIG. 1, process step 172 is implemented in the same manner as process step 153 of FIG. 4B, that is by the momentum module 56 determining fitting a linear track to the incident scattering measurements of the muon. Then, as indicated in process step 173, an incident momentum measurement of the charged particle is determined from the incident trajectory. In the automated system 50, process step 173 is implemented by momentum measurement module 56 in the same manner as process step 154 of method 100.

The exit scattering (not shown) of the charged particle passing through three sets of drift cells arranged on the exit side of an object volume is then measured, as indicated in process step 174. In the automated system 50 of FIG. 1, process step 174 is implemented in the same manner as process steps 151 and 152 of method 100. Thereafter, the exit trajectory of the charged particle is determined from the measured exit scattering, as indicated in process step 175. In the automated system 50 of FIG. 1, process step 175 is implemented in the same manner as process step 153 of FIG. 4B, that is, by the momentum module 56 fitting one or more linear tracks to the exit scattering measurements of the muon. Then, as indicated in process step 176, an incident momentum measurement of the charged particle is determined from the incident trajectory. In the automated system 50, process step 176 is implemented by momentum module 56 in the same manner as process step 154 of method 100.

Finally, the incident and exit momentum measurements are averaged, as indicated in process step 177.

Figure 9:
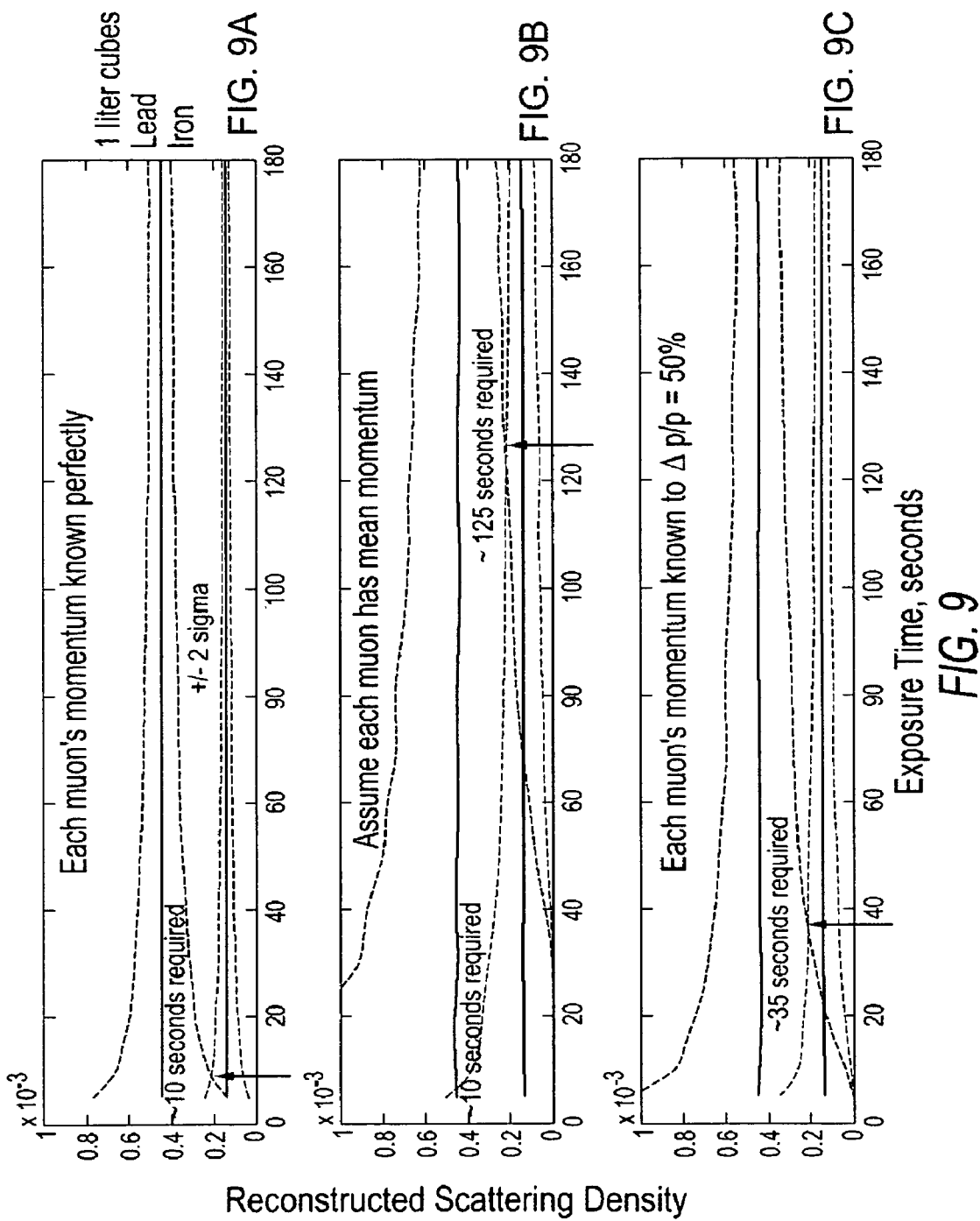
FIG. 9A illustrates graphs of reconstructed scattering density for 1 liter cubes of lead and iron assuming each muon's momentum is known perfectly, showing that these materials may be distinguished at the 2-sigma (97% statistical significance) level after 10 seconds of integration.
FIG. 9B illustrates graphs of reconstructed scattering density for 1 liter cubes of lead and iron assuming each muon has the mean momentum, showing that these materials may be distinguished at the 2-sigma level after 125 seconds of integration.
FIG. 9C illustrates graphs of reconstructed scattering density for 1 liter cubes of lead and iron assuming each muon momentum is known to $\Delta p/p=50\%$, showing that these materials may be distinguished at the 2-sigma level after 35 seconds of integration.

Momentum measurements of the charged particles are particularly useful in reconstructing scattering density of the object under interrogation. To enable appreciation of the benefit of measuring muon momentum, a simple example is presented in which two 1 liter cubes of material, one of iron, and one of lead occupy the volume of the detector of FIG. 2. Referring to FIG. 9, and using a simulated muon flux wherein each muon's momentum is known exactly, we show that, by reconstructing scattering density, we can discriminate the two cubes from one another at a 2 sigma level in about 10 seconds (top plot). However, the variance introduced by the momentum spread of the incident flux significantly decreases the precision of the reconstructions. In the middle plot of FIG. 9, we show that, with no knowledge of muon momentum, the same discrimination requires about 125 seconds of exposure. If, however, we measure muon momentum to about $\Delta p/p$ of 50%, then the exposure time is only about 35 seconds (bottom plot). Uranium has a scattering strength nearly twice that of lead, so that discriminating uranium from iron is significantly faster than discriminating lead from iron, particularly when some (even rather approximate) momentum information is available.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only.

Other variations and modifications of the present invention will be apparent to those of skill in the art, and it is the intent of the appended claims that such variations and modifications be covered.

The description as set forth is not intended to be exhaustive or to limit the scope of the invention. Many modifications and variations are possible in light of the above teaching without departing from the scope of the following claims. It is contemplated that the use of the present invention can involve components having different characteristics.

The invention claimed is:

1. A method for measuring both momentum and trajectory of a charged particle using the same drift cells, said method comprising:
   providing at least three sets of drift cells to obtain at least three positional measurements of a charged particle passing therethrough; said drift cells having sufficient mass to scatter said charged particle to enable the same sets of drift cells to measure both trajectory and momentum entirely from said scattering by said drift cells;
   measuring both trajectory and momentum of said charged particle using said same drift cells; wherein measuring both trajectory and momentum of said charged particle using said same drift cells comprises:
      scattering said charged particle using said at least three sets of plurality of drift cells;
      obtaining at least three positional measurements of said scattering charged particle using said at least three sets of drift cells so as to enable a line fit with a free parameter from which to calculate momentum of said charged particle;
      fitting one or more linear tracks to said at least three positional measurements of said scattering charged particle to determine at least one trajectory thereof; and
      determining the degree of scattering of said charged particle from a goodness of said linear track fit(s) to said at least three positional measurements of said scattering charged particle to determine momentum of said charged particle.

2. The method of claim 1, further comprising:
   providing at least three sets of drift cells arranged on an incident side of an object volume to obtain at least three positional measurements of a charged particle passing therethrough; said drift cells having sufficient mass to incident scatter in the detectors themselves said charged particle in order to measure both incident trajectory and incident momentum of said charged particle using said detectors arranged on said side;
   providing at least three sets of drift cells arranged on an exit side of an object volume to obtain at least three positional measurements of a charged particle passing therethrough, wherein said drift cells have sufficient mass to exit scatter in the drift cells themselves said charged particle in order to measure both exit trajectory and exit momentum of said charged particle using said drift cells arranged on said exit side;
   wherein measuring both trajectory and momentum of said charged particle using said same drift cells comprises:
      scattering said charged particle using said plurality of incident drift cells;
      obtaining at least three positional measurements of said incident scattering charged particle using said three sets of incident drift cells so as to enable a line fit with a free parameter from which to calculate incident momentum;
      fitting one or more linear tracks to said at least three positional measurements of said incident scattering charged particle to determine at least one incident trajectory thereof; and
      determining the incident momentum of said charged particle from a goodness of said linear track fit(s) to said at least three positional measurements of said incident scattering charged particle;
      exit scattering said charged particle using said three sets of drift cells arranged on the exit side;
      obtaining at least three positional measurements of said exit scattering charged particle using said three sets of drift cells arranged on the exit side so as to enable a line fit with a free parameter from which to calculate exit momentum;
      fitting one or more linear tracks to said at least three positional measurements of said exit scattering charged particle to determine at least one exit trajectory thereof; and
      determining the exit momentum of said charged particle from a goodness of said linear track fit(s) to said at least three positional measurements of said exit scattering charged particle.

3. The method of claim 2,
   further comprising
      averaging said incident momentum measurement and said exit momentum measurement in order to reduce noise.

4. The method of claim 1, wherein obtaining at least three positional measurements of said scattering charged particle using said at least three sets of drift cells includes
   detecting drift cells hit by charged particles and corresponding hit times.

5. A system for measuring both momentum and trajectory of a charged particle passing through a detector, said system comprising:
   at least three sets of position sensitive detectors configured to obtain at least three positional measurements of a charged particle passing therethrough; said position sensitive detectors having sufficient mass to scatter said charged particle to enable the same sets of position sensitive detectors to measure both trajectory and momentum entirely from said scattering by said positional sensitive detectors;
   wherein said position sensitive detectors comprise drift cells; and
   a controller, operably coupled to the said charged particle detector, for determining a measurement of both trajectory and momentum of said charged particle using the same position sensitive detectors; said controller being configured to:
scatter said charged particle using said position sensitive detectors;
obtain at least three positional measurements of said scattering charged particle using said at least three sets of position sensitive detectors so as to enable a line fit with a free parameter from which to calculate momentum;
fit one or more linear tracks to said at least three positional measurements of said scattering charged particle to determine at least one trajectory thereof; and
determine the degree of scattering of said charged particle from a goodness of said linear track fit(s) to said at least three positional measurements of said scattering charged particle to determine momentum of said charged particle.

6. The system of claim 5, wherein said plurality of position sensitive detectors are arranged on at least one side of an object volume to be scanned.

7. The system of claim 5, further comprising
at least three sets of position sensitive detectors arranged on an incident side of an object volume to obtain at least three positional measurements of a charged particle passing therethrough; said incident position sensitive detectors having sufficient mass to incident scatter in the detectors themselves said charged particle in order to measure both incident trajectory and incident momentum of said charged particle using said detectors arranged on said incident side;
at least three sets of position sensitive detectors arranged on an exit side of an object volume to obtain at least three positional measurements of a charged particle passing therethrough, wherein said position sensitive detectors have sufficient mass to exit scatter in the detectors themselves said charged particle in order to measure both exit trajectory and exit momentum of said charged particle using said detectors arranged on said exit side;

wherein said controller is configured to:
scatter said charged particle using said plurality of incident position sensitive detectors;
obtain at least three positional measurements of said incident scattering charged particle using said three sets of incident position sensitive detectors so as to enable a line fit with a free parameter from which to calculate incident momentum;
fit one or more linear tracks to said at least three positional measurements of said incident scattering charged particle to determine at least one incident trajectory thereof;
determine the incident momentum of said charged particle from a goodness of said linear track fit(s) to said at least three positional measurements of said incident scattering charged particle;
exit scattering said charged particle using said three sets of position sensitive detectors arranged on the exit side;
obtain at least three positional measurements of said exit scattering charged particle using said three sets of position sensitive detectors arranged on the exit side so as to enable a line fit with a free parameter from which to calculate exit momentum;
fit one or more linear tracks to said at least three positional measurements of said exit scattering charged particle to determine at least one exit trajectory thereof; and
determine the exit momentum of said charged particle from a goodness of said linear track fit(s) to said at least three positional measurements of said exit scattering charged particle.

8. The system of claim 7, wherein said controller is adapted and arranged to:
average said incident momentum measurement and said exit momentum measurement in order to reduce noise.

* * * * *